(12) United States Patent
Tang et al.

(10) Patent No.: US 11,344,594 B2
(45) Date of Patent: May 31, 2022

(54) **USE OF FAT-SOLUBLE EXTRACT OF *BRUCEA JAVANICA L. MERR* IN PREPARING MEDICINES FOR PROMOTING PERIPHERAL NERVE REGENERATION**

(71) Applicant: NANTONG UNIVERSITY, Jiangsu (CN)

(72) Inventors: Xin Tang, Jiangsu (CN); Chunkang Tang, Jiangsu (CN)

(73) Assignee: NANTONG UNIVERSITY, Jiangsu (CN)

( * ) Notice: Subject to any disclaimer, the term of this patent is extended or adjusted under 35 U.S.C. 154(b) by 0 days.

(21) Appl. No.: 17/422,003

(22) PCT Filed: Jun. 19, 2020

(86) PCT No.: PCT/CN2020/097110
§ 371 (c)(1),
(2) Date: Jul. 9, 2021

(87) PCT Pub. No.: WO2021/212635
PCT Pub. Date: Oct. 28, 2021

(65) Prior Publication Data
US 2022/0040247 A1 Feb. 10, 2022

(30) Foreign Application Priority Data
Apr. 21, 2020 (CN) .......................... 202010315841.7

(51) Int. Cl.
*A61K 36/185* (2006.01)

(52) U.S. Cl.
CPC ...... *A61K 36/185* (2013.01); *A61K 2236/333* (2013.01)

(58) Field of Classification Search
None
See application file for complete search history.

(56) References Cited

FOREIGN PATENT DOCUMENTS

| CN | 103989669 A | 8/2014 |
|---|---|---|
| CN | 103239625 B | 9/2014 |
| CN | 108451951 A | 8/2018 |
| CN | 109833377 A | 6/2019 |
| CN | 111494439 A | 8/2020 |
| KR | 20200021880 A | 3/2020 |

OTHER PUBLICATIONS

Wang, Qun, Study on the chemical constituents of the dregs of Brucea Fructus; China Excellent Master's Thesis Full-text Database (Electronic Journal) Medicine and Health Special, ISSN: 1674-0246 E057-266, pp. 53-55, 3.6.4 Flavonoids. Mar. 15, 2017.
Zhao, Ming et al.; Bruceines K and L from the Ripe Fruits of Brucea javanica; Helvetica chimica Acta, vol. 94, No. 11, Nov. 14, 2011, ISSN:1522-2675, pp. 2099-2105.
Wang, Walter et al.; Growth-promoting effects of quercetin on peripheral nerves in rats; The International journal of artificial organs, vol. 34, No. 11, Dec. 15, 2011, ISSN:0391-3998, pp. 1095-1105.
Shi, Gaofeng et al.; Microwave assisted mixed solvent extraction process for total flavonoids from licorice residue Food research and development; vol. 10, No. 32, ISSN: 1005-6521 pp. 43, Nov. 30, 2011.

*Primary Examiner* — Russell G Fiebig
(74) *Attorney, Agent, or Firm* — Novick, Kim & Lee, PLLC; Allen Xue

(57) ABSTRACT

A fat-soluble extract of *Brucea javanica* L. Merr is employed in preparing medicines for promoting peripheral nerve regeneration. The fat-soluble extract of *Brucea javanica* L. Merr is obtained by extraction with a mixed solution of absolute ethanol and ethyl acetate. The present invention finds through research that the fat-soluble extract of *Brucea javanica* L. Merr promotes the growth of peripheral DRG neurons and neurites, and promotes the division and proliferation of the glial cells, that is, Schwann cells, of the peripheral nervous system, suggesting that the fat-soluble extract of *Brucea javanica* L. Merr has the effect of promoting peripheral nerve regeneration.

8 Claims, 4 Drawing Sheets

USE OF FAT-SOLUBLE EXTRACT OF *BRUCEA JAVANICA L. MERR* IN PREPARING MEDICINES FOR PROMOTING PERIPHERAL NERVE REGENERATION

BACKGROUND

Technical Field

The present invention relates to the technical field of biomedicine, and specifically to a fat-soluble extract of *Brucea javanica* L. Merr, which comprises ingredients promoting peripheral nerve regeneration

Related Art

*Brucea javanica* L. Merr, a plant of family Simaroubaceae, is a small tree plant or deciduous shrub with a height of about 2 m, which is mainly distributed in the tropics and subtropics of the southern coastal areas of China, such as Hainan, Guangdong, Guangxi and Yunnan. The dry and ripe fruit of *Brucea javanica* L. Merr has a gray-black, hard and brittle shell, and an overall oblong oval shape that is 6-10 mm long and has slightly pointed ends. After being broken open, yellow-white seed kernels in an oval shape that are 4-7 mm long and 3-5 mm in diameter, are exposed. The seed kernels are smooth and oily, odorless, tasted extremely bitter, and cold in nature. Traditional Chinese medicine science considers that the main functions of *Brucea javanica* L. Merr include clearing away heat and detoxification, preventing malaria, stopping diarrhea, and wart corrosion. *Brucea javanica* L. Merr is recorded in the "Records of Tradition Chinese and Western Medicine in Combination" to treat malaria, in "Chinese Herbal Medicine of Guangxi" to treat early schistosomiasis and hemorrhoids, and in "Supplement to Compendium of Materia *Medica*" to treat warts. In recent years, the research is focused on its good anti-tumor effects.

The main chemical components in *Brucea javanica* L. Merr of family Simaroubaceae include Nigakilactones, flavonoids, triterpenoids and alkaloids. Nigakilactones are characteristic components of *Brucea* plants, and are also the effective components. They mainly include: Bruceines A-H, Brusatol, Bruceosides A-G, Javanicosids A-L, Javanicolids A-D, Brucamarin, and Brucedic acid, etc. Nigakilactone compounds usually have potent anti-tumor, anti-malarial and anti-inflammatory activities. Brusatol, dihydrobrusatol, Bruceosides, and dihydrobruceosides isolated from Nigakilactone compounds are water-soluble and bitter components and are the main research objects of many scholars. It is worth noting that water-soluble Nigakilactone compounds are also considered to be the material basis for the main toxicity of *Brucea javanica* L. Merr.

The oil from *Brucea javanica* L. Merr seeds is believed to have anti-tumor effects in traditional herbal medicine science. The biologically active components in *Brucea javanica* L. Merr oil mainly comprises oleic acid, linoleic acid, tetracyclic triterpenoids and anthraquinones. The fatty acid composition mainly includes palmitic acid, stearic acid, oleic acid, and linoleic acid. There are no reports on the toxicity of such components. Studies have shown that the apoptotic effect of *Brucea javanica* L. Merr is mainly effected through the mitochondrial pathway and death receptor signaling pathway, by suppressing cell growth by inhibiting the G0/G1 cell cycle. The main ingredients in the commonly used oil emulsion oral liquid and injection of *Brucea javanica* L. Merr are refined *Brucea javanica* L. Merr oil, and refined soybean lecithin and glycerin, which are used in the clinical adjuvant treatment of lung cancer, brain metastases of lung cancer, gastrointestinal tumors and liver cancer.

At present, the research on *Brucea javanica* L. Merr of family Simaroubaceae mostly focuses on its anti-tumor effect or dermatological wart corrosion. There is no report about the use of *Brucea javanica* L. Merr or main components thereof in the treatment of nervous system-related diseases.

SUMMARY

The present invention finds through research that the fat-soluble extract of *Brucea javanica* L. Merr can promote the growth of peripheral DRG neurons and neurites, and promote the division and proliferation of the glial cells, that is, Schwann cells, of the peripheral nervous system, suggesting that the fat-soluble extract of *Brucea javanica* L. Merr has the effect of promoting peripheral nerve regeneration.

The following specific technical solution is adopted in the present invention.

Use of a fat-soluble extract of *Brucea javanica* L. Merr in preparing medicines for promoting peripheral nerve regeneration is provided.

The fat-soluble extract of *Brucea javanica* L. Merr according to the present invention comprises active ingredients obtained by extraction with a mixed solution of absolute ethanol and ethyl acetate. Preferably, the percentage by volume of the absolute ethanol in the mixed solution is 45%-85%, and more preferably 75%.

Further, ultrasonic extraction can be used. Preferably, the ultrasonic frequency is 20 kHz, the power is 750 W, the time is 60 min, and the material-to-liquid ratio is 1:5 g/mL.

The effective dose of the fat-soluble extract of *Brucea javanica* L. Merr according to the present invention is 5-30 mg/kg, and more preferably 15 mg/kg.

The present invention investigates the effect of the fat-soluble extract of *Brucea javanica* L. Merr according to the present invention on the growth of nerve cells. The results show that when the cells are cultured in vitro at a concentration of 20 ng/mL, an effect of promoting the growth of nerve cells is initially exhibited. As the concentration increases, the effect gradually become stronger, and the most significant effect is showed when the concentration is 100 ng/mL. However, significant disruption of peripheral DRG neurons and neurites and inhibition of Schwann cell proliferation occur at a concentration of 500 ng/mL. The specific mechanism of action is currently not very clear.

The present invention further investigates the promotion of the fat-soluble extract of *Brucea javanica* L. Merr on the recovery of sciatic nerve function. The results show that when the fat-soluble extract of *Brucea javanica* L. Merr is added at a dosage of 5-30 mg/kg to a silicone tube in the injured area in a rat sciatic nerve defect model, the recovery of sciatic nerve function is promoted. The most preferred effective dose is 15 mg/kg. However, as the dosage is increased to 45 mg/kg, there is no significant difference in the recovery of sciatic nerve function compared with the negative control group with normal saline. It further indicates that the fat-soluble extract of *Brucea javanica* L. Merr can achieve the result of promoting peripheral nerve regeneration in animals only at an appropriate dosage.

The present invention has the following advantages.

The present invention finds for the first time that the fat-soluble extract of *Brucea javanica* L. Merr, especially the fat-soluble extract extracted with a mixed solution of anhydrous ethanol and ethyl acetate in a certain proportion combined with ultrasonic extraction, has the ability to promote the growth of peripheral DRG neurons and neurites cultured in vitro and the proliferation of peripheral Schwann cells in a specific dosage range.

The present invention further investigates the promotion of the fat-soluble extract of *Brucea javanica* L. Merr on the recovery of sciatic nerve function in a rat sciatic nerve defect model. The results confirm that the fat-soluble extract of *Brucea javanica* L. Merr has the effect of promoting peripheral nerve regeneration in a specific dosage range.

Experimental results show that the most preferred effective concentration range for in-vitro cell culture is 20-100 ng/mL, and the most preferred in-vivo effective dose range in a rat sciatic nerve injury model is 5-30 mg/kg. The new finding of the present invention about the effect of the fat-soluble extract of *Brucea javanica* L. Merr provides a new research direction for clinical treatment of nervous system related diseases, particularly peripheral nerve regeneration.

BRIEF DESCRIPTION OF THE DRAWINGS

(FIG. 2A shows the immunohistochemical staining of axon growth of DRG neurons promoted by various dosages of the fat-soluble extract of *Brucea javanica* L. Merr; and FIG. 2B is a histogram showing the statistical result of growing axon length of DRG neuron promoted by various dosages of the fat-soluble extract of *Brucea javanica* L. Merr.

(FIG. 3A shows the EdU staining of Schwann cell proliferation promoted by various dosages of the fat-soluble extract of *Brucea javanica* L. Merr; and FIG. 3B is a histogram showing the statistical result of Schwann cell proliferation promoted by various dosages of the fat-soluble extract of *Brucea javanica* L. Merr.

DETAILED DESCRIPTION

Figure 1:
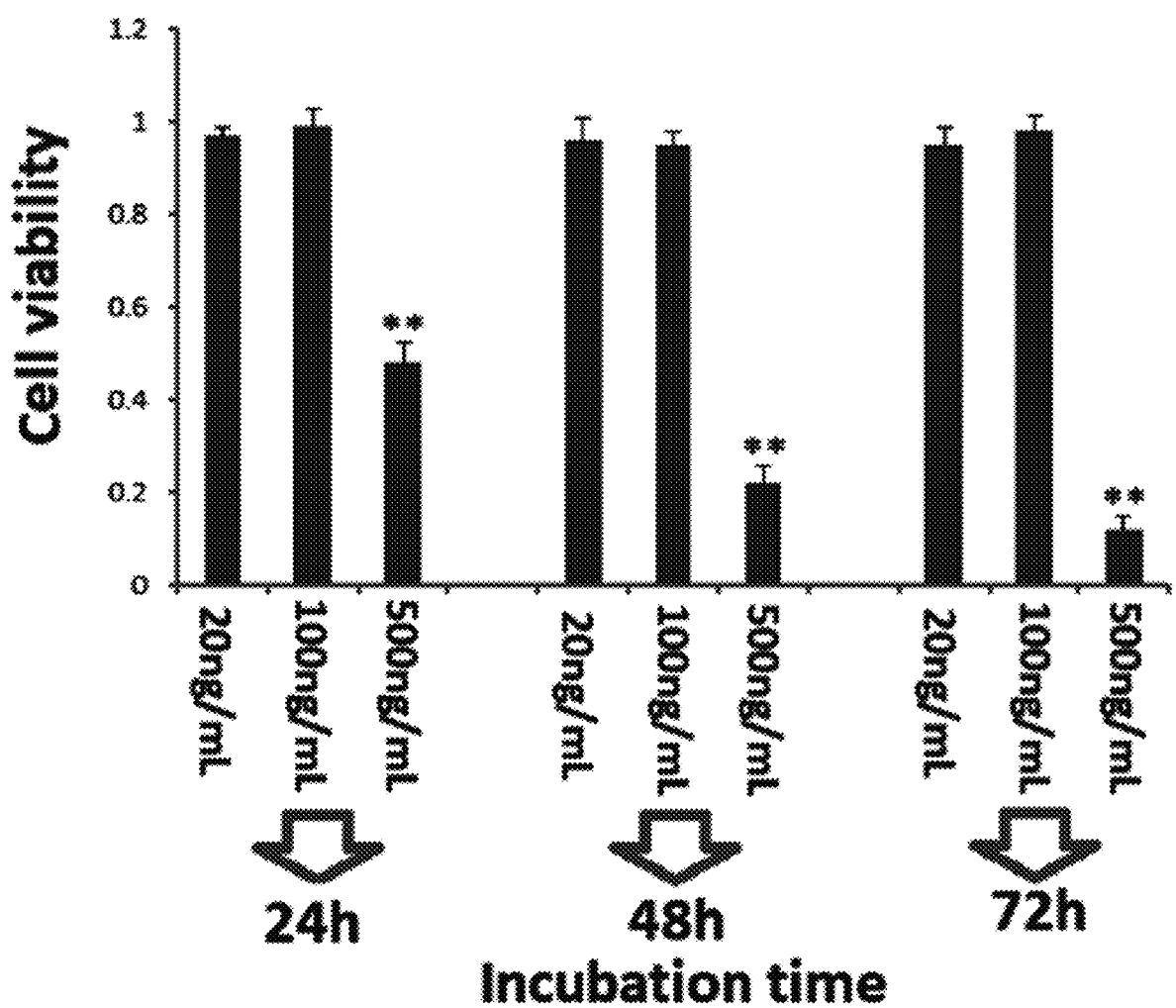
FIG. 1 shows the cytotoxicity of the fat-soluble extract of *Brucea javanica* L. Merr detected by CCK8.

Specific steps of the present invention are described below based on embodiments, but the present invention is not limited to the embodiments.

The terms used in the present invention, unless otherwise stated, generally have the meaning commonly understood by a person of ordinary skill in the art.

The present invention is further described below in detail with reference to specific examples and data. It should be understood that the embodiments are only for describing the present invention by using examples, but do not limit the scope of the present invention in any manner.

In the following embodiments, various processes and methods that are not described in detail are common conventional methods in the art.

Example 1. Preparation of the Fat-Soluble Extract of *Brucea javanica* L. Merr

*Brucea javanica* L. Merr of family Simaroubaceae, purchased from the traditional Chinese medicine (TCM) pharmacy of Nantong Hospital of Traditional Chinese Medicine, was washed with deionized water, dried in an oven at 60-65° C. for 2 days and then ground into powder (300 g). 50 g of dry *Brucea javanica* L. Merr powder was accurately weighed, fed to an extraction vessel, and soaked in mixed solutions of absolute ethanol and ethyl acetate at different concentrations at room temperature (22° C.) for 48 hrs. Groups: 95% absolute ethanol+5% ethyl acetate; 85% absolute ethanol+15% ethyl acetate; 75% absolute ethanol+25% ethyl acetate; 65% absolute ethanol+35% ethyl acetate; 55% absolute ethanol+45% ethyl acetate; 45% absolute ethanol+55% ethyl acetate; 35% absolute ethanol+65% ethyl acetate; 25% absolute ethanol+75% ethyl acetate; 15% absolute ethanol+85% ethyl acetate; 5% absolute ethanol+95% ethyl acetate. The soak solutions of various concentrations were further ultrasonically extracted at an ultrasonic frequency of 20 kHz, a power of 750 W, and a material-to-liquid ratio of 1:5 g/mL for a time of 60 min. The resulting solutions were filtered through Whatman No. 1 filter paper, and then evaporated in a rotary evaporator (Buchi rotavapor R-124) under reduced pressure and concentrated at 40° C. After most of the solvent was removed, the extract fractions A (about 18-23 g) of *Brucea javanica* L. Merr seeds extracted with different extraction solutions were obtained, and stored in a refrigerator at −20° C. for later use.

Example 2. Extraction Effect of Mixed Solutions of Absolute Ethanol and Ethyl Acetate at Different Concentrations In order to detect the effect of the fat-soluble extract of *Brucea javanica* L. Merr extracted with various concentrations of absolute ethanol and ethyl acetate on the growth of nerve cells, the nerve cell line PC12 cells were used as the observation model in the experiment.

PC12 cells were cultured in DMEM complete medium (containing 10% horse serum, 5% fetal bovine serum, 100 U/ml penicillin, and 100 µg/ml streptomycin) in a culture dish which was placed in an incubator at 5% $CO_2$ and 37° C. The medium was refreshed every two days and the cells were subcultured when grown to 80% confluence. In the experiment, PC12 cells in logarithmic growth phase were inoculated at $5 \times 10^4$/ml into a 24-well culture plate in 400 µl per well. After 24 hrs, the medium was replaced by a DMEM medium containing 1% horse serum and 1% fetal bovine serum. In the experiment, a negative control group with DMEM medium comprising 1% horse serum and 1% fetal bovine serum, and experimental groups treated with 100 ng/mL extract obtained by extraction with a mixed solution of different concentrations of absolute ethanol and ethyl acetate, were respectively set. After 3-d culture with the extract, the morphological changes of PC12 cells were observed under an inverted microscope. 50 cells were randomly selected from each group, and the positive cell rate, axon length and number of axons were measured.

The results in Table 1 show that after the PC12 cells are treated 3 days with the fat-soluble extracts of *Brucea javanica* L. Merr prepared by using mixed solutions of absolute ethanol and ethyl acetate at different concentrations, the extract prepared by using a combination of 75% absolute ethanol+25% ethyl acetate has the most significant effect of promoting the growth and differentiation of nerve cells (**$p<0.01$*$p<0.05$) with respect to the positive cell rate, axon length and number of axons, compared with the negative control group with DMEM medium containing 1% horse serum and 1% fetal bovine serum. It is suggested that 75% absolute ethanol+25% ethyl acetate is the most preferred concentration combination for extraction.

TABLE 1

Effects of extracts prepared by using mixed solutions of absolute ethanol and ethyl acetate at different concentrations on PC12 cells

| Experimental group | Positive cell rate/% | Axon length/μm | Number of axons |
|---|---|---|---|
| Control | 0.08 ± 0.05 | 7.50 ± 0.82 | 0.61 ± 0.30 |
| 95% absolute ethanol + 5% ethyl acetate | 0.09 ± 0.02 | 7.81 ± 0.98 | 0.82 ± 0.11 |
| 85% absolute ethanol + 15% ethyl acetate | 0.22 ± 0.08 | 9.22 ± 1.42 | 121 ± 0.12* |
| 75% absolute ethanol + 25% ethyl acetate | 0.85 ± 0.09** | 22.48 ± 2.05** | 2.82 ± 0.31** |
| 65% absolute ethanol + 35% ethyl acetate | 0.42 ± 0.11* | 12.34 ± 1.64* | 0.93 ± 0.28 |
| 55% absolute ethanol + 45% ethyl acetate | 0.23 ± 0.13 | 10.52 ± 1.67 | 0.91 ± 0.25 |
| 45% absolute ethanol + 55% ethyl acetate | 0.21 ± 0.12 | 8.98 ± 1.32 | 0.89 ± 0.32 |
| 35% absolute ethanol + 65% ethyl acetate | 0.17 ± 0.06 | 8.21 ± 1.42 | 0.81 ± 0.15 |
| 25% absolute ethanol + 75% ethyl acetate | 0.13 ± 0.07 | 7.98 ± 0.95 | 0.79 ± 0.23 |
| 15% absolute ethanol + 85% ethyl acetate | 0.11 ± 0.07 | 7.62 ± 1.12 | 0.71 ± 0.23 |
| 5% absolute ethanol + 95% ethyl acetate | 0.06 ± 0.05 | 7.55 ± 0.92 | 0.51 ± 0.38 |

Example 3. Cytotoxicity Test of the Fat-Soluble Extract of *Brucea javanica* L. Merr The fat-soluble extract of *Brucea javanica* L. Merr prepared in Example 1 was lyophilized overnight (EYELA FDU-1200, Tokyo), and the prepared powder was fed to a 15 ml centrifuge tube and stored at 4° C. A 10 μg/mL solution was formulated in sterile deionized water, and centrifuged at 8000 g for 10 min. Then the solution was diluted to each concentration required in the experiment, and then sterilized by filtering through a 0.2 mm nylon syringe filter (Millipore, USA) for cytotoxicity test in culturing PC12 cell line. The CCK8 kit was purchased from Dojindo Laboratories, Japan.

PC12 cells in the logarithmic growth phase were digested, counted and then re-suspended. The cells were adjusted to have a density of $5\times10^5$/mL, and inoculated in a 96-well plate in 100 μL per well. After the cells were attached to the wall, the medium was discarded, and the cells were wash with 0.01 M PBS for 5 min (×2). The negative control group was a group treated with a DMEM medium containing 1% horse serum and 1% fetal bovine serum. The fat-soluble extract of *Brucea javanica* L. Merr in different concentrations of 20 ng/mL, 100 ng/mL and 500 ng/mL was added to each experimental group. and the cells were cultured for 24 hrs, 48 hrs and 72 hrs respectively. The medium was gently discarded, 10% CCK8 in medium was added in an amount of 100 μL CCK8 per well (that is, 10 μl of CCK8 per 100 μl of medium was added), and the cells were continuously cultured for 2 hrs. The absorbency (OD value) of each group was measured on a microplate reader at 450 nm. The relative survival rate (%) was calculated according to the following formula: Relative survival rate (%)=[(OD of experimental group−OD of blank group)/(OD of control group−OD of blank group)]×100%. Each group had 8 replicates.

FIG. 1 shows the cytotoxicity test result of the fat-soluble extract of *Brucea javanica* L. Merr detected by CCK8. The test results by CCK8 show that the fat-soluble extract of *Brucea javanica* L. Merr at a low concentration of 20 ng/mL and a medium concentration of 100 ng/mL has no obvious cytotoxicity within 72 hours of experimental observation, while the fat-soluble extract of *Brucea javanica* L. Merr at a high concentration of 500 ng/mL shows a significant cytotoxicity from the experimental observation timepoint of 24 hrs compared with the culture with the low concentration 20 ng/mL and the medium concentration 100 ng/mL, suggesting that high concentration of the fat-soluble extract of *Brucea javanica* L. Merr is cytotoxic to nerve cells. The vertical coordinate shows the cell viability of PC12 cells cultured with each concentration of the fat-soluble extract of *Brucea javanica* L. Merr in the experimental group, which is expressed in viability percentage of PC12 cells cultured in the negative control group with DMEM medium containing 1% horse serum and 1% fetal bovine serum. **$p<0.01$.

Example 4. Effect of the Fat-Soluble Extract of *Brucea javanica* L. Merr on the Axon Growth of DRG Neurons SD rats at 15 days of pregnancy were narcotized by intraperitoneally injecting with 10% chloral hydrate (0.2 mL/100 g), shaved, and disinfected by spraying 75% alcohol. The embryo was taken out of the womb and placed in a sterile dish filled with pre-cooled D-Hank's medium. Then the dish was placed on ice, the dorsal root ganglia was removed under a dissecting microscope, and the fascia on the surface of the ganglia was peeled off as much as possible. The dorsal root ganglia were cut to have a size of about 0.5 mm$^3$ by ophthalmic scissors, digested with 0.25% trypsin at 37° C. for 15 min, and then terminated with serum. After centrifugation, the single-cell suspension was inoculated at a cell density of $5\times10^5$/mL in a 24-well plate fitted with glass slides and pre-coated with PDL. The system was placed in an incubator at 37° C., and 5% $CO_2$, and the cells were incubated with 10% FBS and 90% DMEM. After the cells were attached, the cells in the negative control group were cultured with 97% Neurobasal+2% B27+1% GluMAX medium. The fat-soluble extract of *Brucea javanica* L. Merr in different concentrations of 20 ng/mL, 100 ng/mL and 500 ng/mL was respectively added to each experimental group, and the DRG neurons were continuously cultured for 72 hrs.

After the DRG neurons were cultured for 72 hours according to the above method, the medium was aspirated, and the cells were washed once with 0.01 M PBS. 500 μL of 4% paraformaldehyde was added, and the cells were fixed at room temperature for 30 min. The fixative was removed, and the cells were washed with 0.01 M PBS for 10 min (×3) at room temperature. The plate was blocked with 0.01 M PBS containing 10% goat serum and 0.3% Triton X-100 at 37° C. for 60 min, and then the blocking buffer was removed.

Fluorescence immunocytochemical analysis: The primary antibody (goat anti-GAP-43 polyclonal antibody, 1:200) was dripped, stood overnight at 4° C., and washed with 0.01M PBS for 10 min (×3). The secondary antibody (FITC donkey anti-goat IgG, 1:200) was dripped, and the cell nucleus was labeled with Hoechst33342 (5 μg/ml), stood at room temperature for 1 hr in the dark. The cells were then washed with 0.01M PBS for 10 min (×3). A blank control group without primary antibody was set in the experiment. For the blank control group, the steps were the same as above except that in the step (3), the goat anti-GAP-43 polyclonal antibody was replaced by 0.01 M PBS. Under a laser confocal microscope (FITC excitation wavelength: 488 nm, observation wavelength: 500-535 nm; Hoechst33342 argon-ion Ar excitation wavelength: 353-364 nm, observation wavelength: 460-480 nm), the results of fluorescence immunocytochemical detection were observed.

Figure 2A:
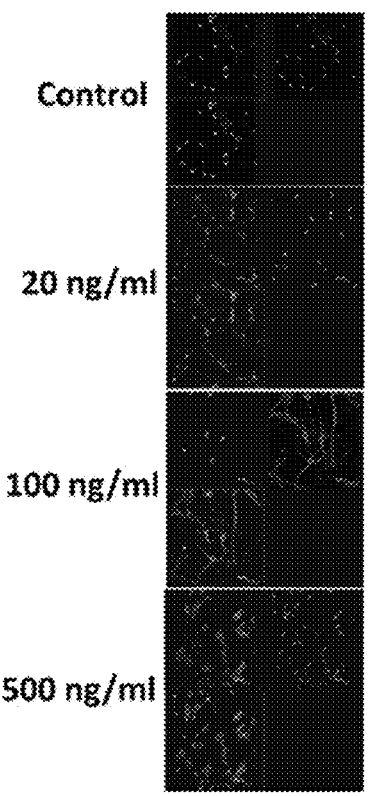
FIGS. 2A and 2B show the effect of the fat-soluble extract of *Brucea javanica* L. Merr on the axon growth of DRG neurons detected by immunohistochemistry.
Figure 2B:
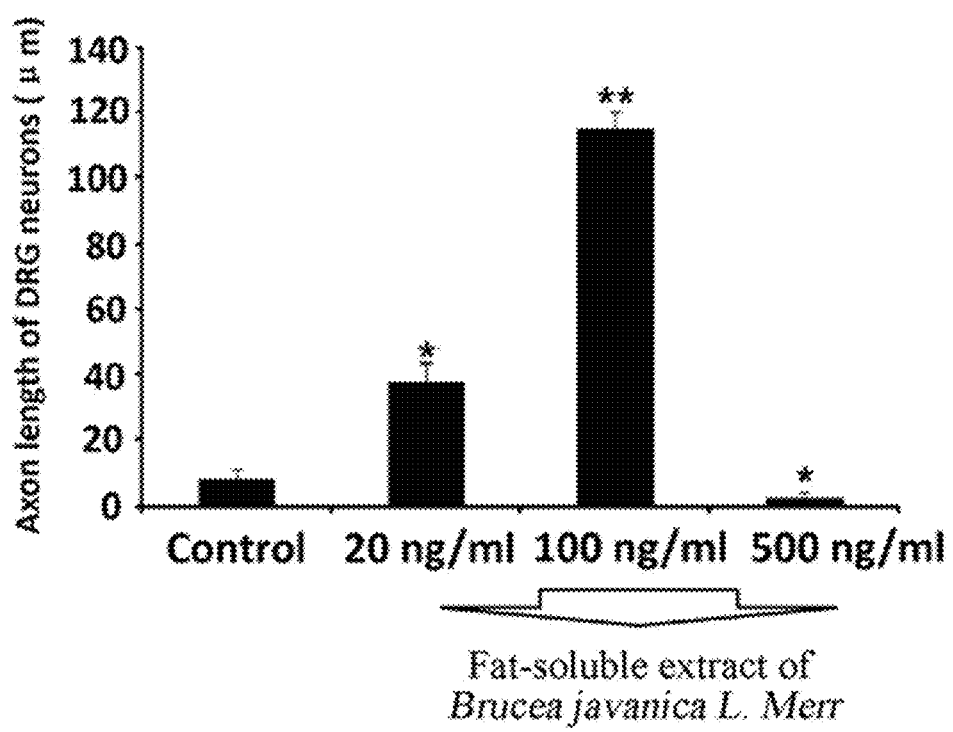

FIGS. 2A and 2B show the effect of the fat-soluble extract of *Brucea javanica* L. Merr on the axon growth of DRG neurons detected by immunohistochemistry. (FIG. 2A shows the immunohistochemical staining of axon growth of DRG neurons promoted by various dosages of the fat-soluble extract of *Brucea javanica* L. Merr; and FIG. 2B is a histogram showing the statistical result of growing axon length of DRG neuron promoted by various dosages of the fat-soluble extract of *Brucea javanica* L. Merr. The results in FIGS. 2A and 2B shows that compared with the negative control group treated with 97% Neurobasal+2% B27+1% GluMAX medium and DRG neurons cultured with a low concentration of the extract, when the concentration of the fat-soluble extract of *Brucea javanica* L. Merr. is 100 ng/ml, the number and length of axons marked with GAP-43 of DRG neurons increase significantly. The fat-soluble extract of *Brucea javanica* L. Merr at a high concentration of 500 ng/ml has no promotion on DRG neurons, and the growth promotion effect is even lower than the fat-soluble extract of *Brucea javanica* L. Merr. at a low concentration of 20 ng/ml. It is suggested that the fat-soluble extract of *Brucea javanica* L. Merr at an appropriate medium concentration of 100 ng/ml can significantly promote the axon growth of DRG neurons (**$p<0.01$*$p<0.05$).

Example 5: Effect of the Fat-Soluble Extract of *Brucea javanica* L. Merr on the Proliferation of Schwann Cells 1. Culture and Purification of Schwann Cells 1-2 day-old newborn SD rats were freeze narcotized and disinfect with 75% alcohol. The sciatic nerve was exposed and isolated through the posterolateral femoral muscle space, and soaked in pre-cooled HBSS solution. The epineurium was carefully removed under a dissecting microscope. The sciatic nerve was cut in 200 μl of 1 mg/ml collagenase, digested for 30 min at 37° C. The collagenase was removed, and 0.125% trypsin was added for digestion at 37° C. for 12 min. The digestion was terminated, the system was centrifuged and the supernatant was discarded. The cells were inoculated at a cell density of $1\times10^6$ to a plate pre-coated with PDL, and incubated in an incubator at 37° C. and 5% $CO_2$. The medium was replaced by a medium containing cytarabine (1:1000) within 24 hrs. The cells were purified after growth to 80% confluence. The cells were digested into a cell suspension with 0.125% trypsin, and then terminated with serum. Anti-thy1.1 (1:1000) was added and the cells were incubated on ice for 2 hrs. After centrifugation, the supernatant was discarded. A mixed solution containing 250 μl of rabbit complement and 750 μl of DMEM medium (1:3) was added and the cells were incubated at 37° C. for 1 hr. The cells were re-suspended and then inoculated at a cell density of $3\times10^5$ to a plate pre-coated with PDL. Moreover, 2 μM forsokolin and 10 ng/ml HRG were added to the dish, and the medium was refreshed every 3 days.

2. Detection of Cell Proliferation by EdU

Schwann cells in the 96-well plate were treated for 24 hrs with the fat-soluble extract of *Brucea javanica* L. Merr at a different concentration of 20 ng/mL, 100 ng/mL, and 500 ng/mL. The cells were detected with the Cell-Light™ EdU DNA cell proliferation kit available from Guangzhou Ribo-Bio Company following the experimental operation in the manual. The EdU solution (reagent A) was diluted with the cell culture medium at a ratio of 1:1000 to prepare an appropriate amount of 50 μM EdU medium. 100 μL of 50 μM EdU medium was added to each well and the cells were incubated at 37° C. for 2 hrs. The medium was discarded, and the cells were washed with PBS for 5 min (×3). 50 μL of 4% paraformaldehyde was added to each well to fix the cells for 15 min at room temperature, and then the fixative was discarded. 50 μL of 2 mg/mL glycine was added to each well and the cells were incubated for 5 min. The glycine solution was discarded, and the cells were washed with PBS for 5 min (×3). 100 μL of a penetrant (0.5% TritonX-100 in PBS) was added to each well and the cells were incubated for 10 min. The cells were washed with PBS for 5 min (×3). 100 μL of 1× Apollo® staining reaction solution was added to each well, and the cells were incubated for 30 min in the dark at room temperature. The staining reaction solution was discarded. 100 μL of a penetrant (0.5% TritonX-100 in PBS) was added and the cells were washed on a decolorizing shaker for 10 min (×3). The penetrant was discarded. 100 μL of methanol was added to each well and the cells were washed for 5 min (×3). 5 μg/mL Hoechst 33342 reaction solution was added and the cells were incubated for 30 min. The staining reaction solution was discarded and the cells were washed with PBS for 10 min (×3). 5 low-magnification fields of each sample at 20× magnification were randomly selected, and the images were collected Leica DC 300 and analyzed by Leica QW in analysis software.

Figure 3A:
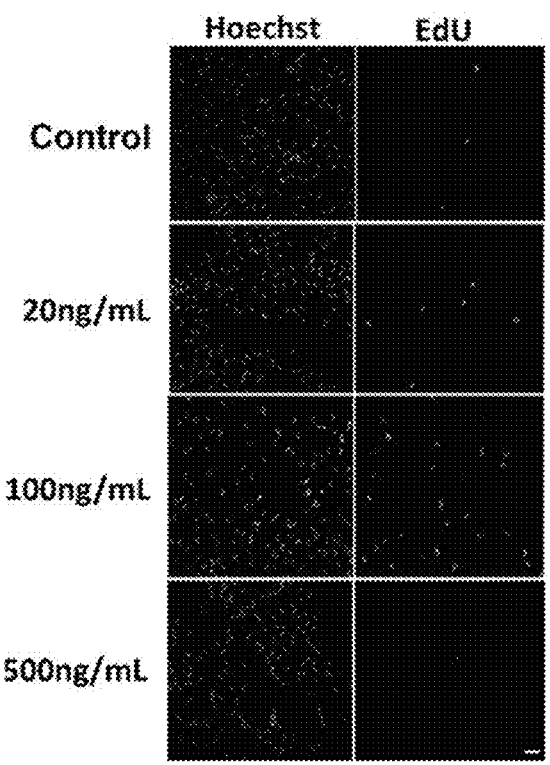
FIGS. 3A and 3B show EdU staining to detect the effect of the fat-soluble extract of *Brucea javanica* L. Merr on the proliferation of Schwann cells.
Figure 3B:
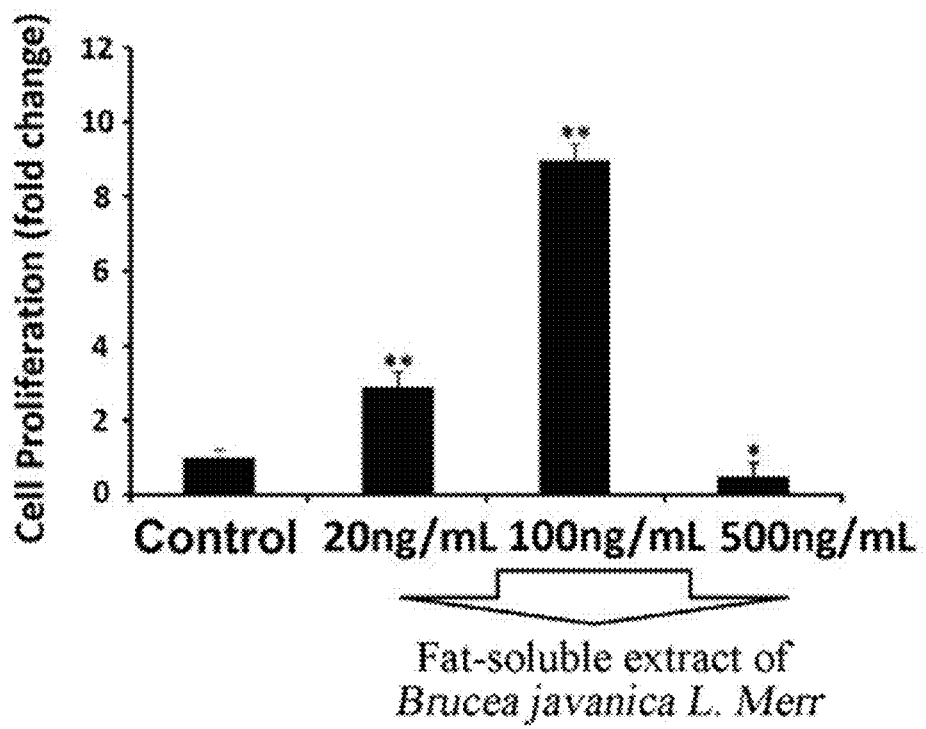

FIGS. 3A and 3B show EdU staining to detect the effect of the fat-soluble extract of *Brucea javanica* L. Merr on the proliferation of Schwann cells. (FIG. 3A shows the EdU staining of Schwann cell proliferation promoted by various dosages of the fat-soluble extract of *Brucea javanica* L. Merr: and FIG. 3B is a histogram showing the statistical result of Schwann cell proliferation promoted by various dosages of the fat-soluble extract of *Brucea javanica* L. Merr. The results show that for the cultured primary Schwann cells treated with different concentrations of the fat-soluble extract of *Brucea javanica* L. Merr, the fat-soluble extract of *Brucea javanica* L. Merr at a concentration of 100 ng/ml can significantly promote the proliferation of Schwann cells compared with the negative control group and the group treated with a low concentration of 20 ng/ml; however, when the concentration is 500 ng/ml, it has a significant inhibitory effect on the proliferation of Schwann cells, suggesting that the fat-soluble extract of *Brucea javanica* L. Merr can significantly promote the proliferation of Schwann cells at an appropriate concentration of 100 ng/ml (Scale bar 20 μm). (**$p<0.01$*$p<0.05$).

Example 6. Promotion of the Fat-Soluble Extract of *Brucea javanica* L. Merr on the Recovery of Nerve Function in Rat Sciatic Nerve Defect Model Animal experiment and groups: SD rats were randomly divided into 4 groups (9 in each group), including a negative control group with saline, and experimental groups with different dosages of the fat-soluble extract of *Brucea javanica* L. Merr, including 5 mg/kg, 15 mg/kg, 30 mg/kg and 45 mg/kg. Model preparation and drug treatment: A compound anaesthetic agent (0.2-0.3 ml/100 g) was intraperitoneally injected for anesthesia, and the surgical area of the left femur was routinely shaved, disinfected, and draped. A median incision was made at the back of the left thigh. The skin and fascia were cut in sequence, the sciatic nerve was fully exposed to form a 10 mm defect, and the sciatic nerve was bridged with a silicone tube. The control, namely, saline, was added to a silicone tube to serve as the negative control group, and 5 mg/kg, 15 mg/kg, 30 mg/kg and 45 mg/kg of the fat-soluble extract of *Brucea javanica* L. Merr were respectively added to the experimental groups. The incision was closed by routine suture. The model preparation and subsequent breeding and observations were all carried out in an SPF-grade barrier system.

Sciatic nerve function index (SFI) is an intuitive and reliable indicator used to evaluate the sciatic nerve regeneration and nerve function recovery. Footprint experiments were performed at 4 W, 8 W and 12 W after surgery. The rats were kept in a passage with a width of about 15 cm, a height of about 15 cm, and a length of about 80 cm. The white rice paper was folded to have the same length and width as the passage, and placed at the bottom of the wooden passage. The two hindfeet of rats were dipped in red ink, and then they were transferred to one end of the passage. The rats walked to the other end of the passage by themselves, leaving 4-5 footprints by each foot on the rice paper. The footprints at the clear normal side and the operation side were selected, and the toe spreads (including normal toe spread, NTS; and experimental toe spread, ETS), print length (including normal print length, NPL; and experimental print length, NPL), and intermediary toe spreads (including normal intermediary toe spread, NIT; and experimental intermediary toe spread, EIT) were measured. An SFI value of 0 indicates normal, and an SFI value of −100 indicates complete nerve disconnection. The SFI value is calculated according to a formula below:

$$SFI=-38.3\times[(EPL-NPL)/NPL]+109.5\times[(ETS-NTS)/NTS]+13.3\times[(EIT-NIT)/NIT]-8.8$$

Figure 4:
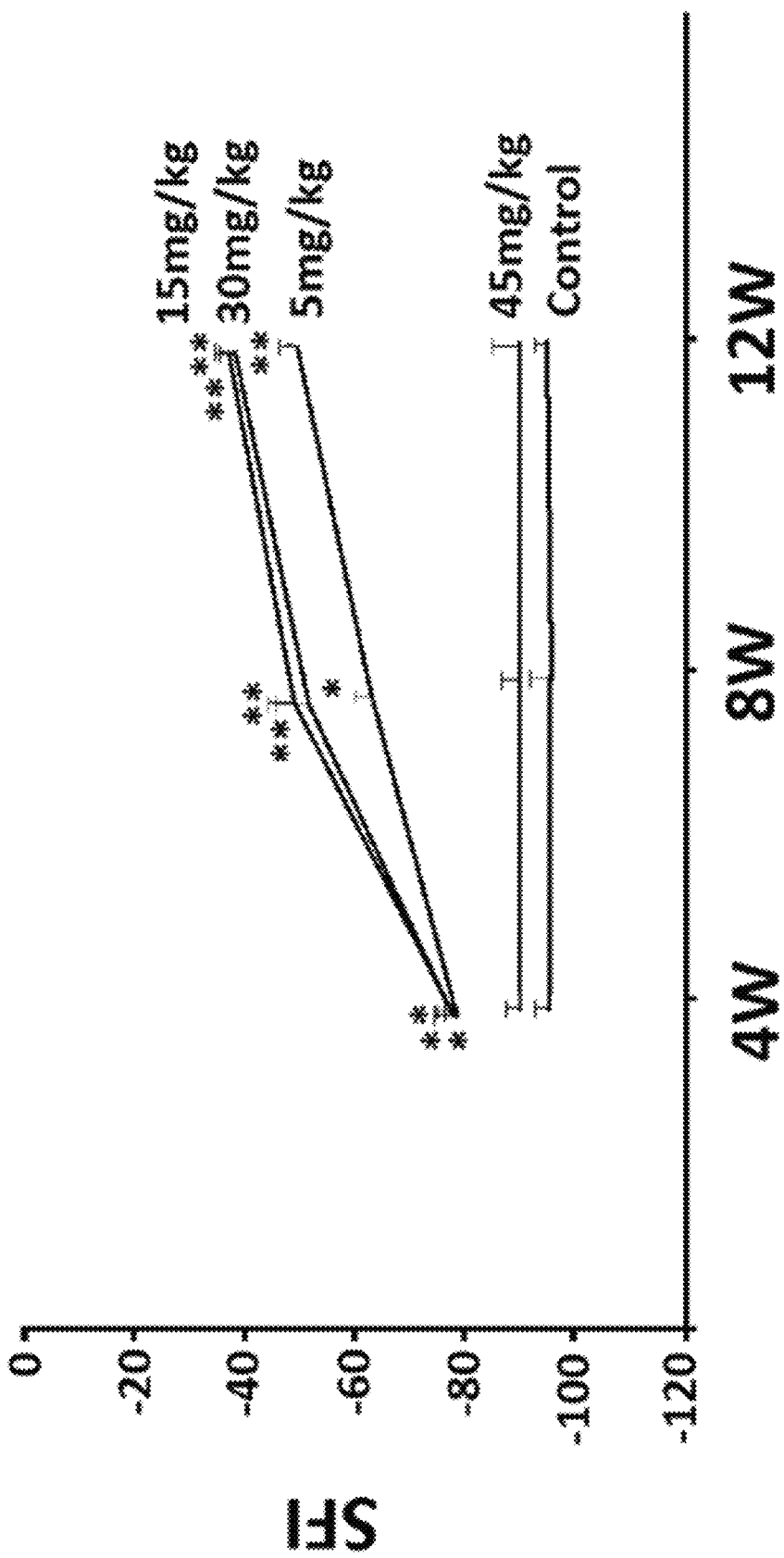
FIG. 4 shows the sciatic nerve function index in a rat sciatic nerve defect model after the fat-soluble extract of *Brucea javanica* L. Merr is applied.

FIG. 4 shows the sciatic nerve function index in a rat sciatic nerve defect model after different concentrations of the fat-soluble extract of *Brucea javanica* L. Merr are applied. The results show that a promotion on the recovery of nerve function is shown at a low dose of 5 mg/kg, the most significant effect of promoting the recovery of nerve function is achieved at a medium dose of 15 mg/kg, and a dose of 30 mg/kg still falls within the most preferred dose range, which all have significant effect than the negative control group with saline. However, there is no significant difference between the group treated with a high dosage of 45 mg/kg and the negative control group with saline. The most preferred dosage of the fat-soluble extract of *Brucea javanica* L. Merr in vivo to promote peripheral nerve regeneration is 15 mg/kg. (**$p<0.01$*$p<0.05$).

The invention claimed is:

1. A method of promoting peripheral nerve regeneration in a subject in need thereof, comprising: administering to the subject an effective dosage of fat-soluble extract of *Brucea javanica* L. Merr.

2. The method of claim 1, wherein the fat-soluble extract of *Bruceajavanica* L. Merr is obtained by extraction with a mixed solution of absolute ethanol and ethyl acetate.

3. The method of claim 2, wherein in the mixed solution of absolute ethanol and ethyl acetate, a volume percentage of absolute ethanol is 45%- 85%.

4. The method of claim 3, wherein in the mixed solution of absolute ethanol and ethyl acetate, the volume percentage of absolute ethanol is 75%.

5. The method of claim 2, wherein the extraction is ultrasonic extraction.

6. The method of claim 5, wherein the ultrasonic extraction is carried out at an ultrasonic frequency of 20 kHz, a power of 750 W for 60 min.

7. The method of claim 1, wherein the effective dosage of the fat-soluble extract of *Bruceajavanica* L. Merr is 5-30 mg/kg.

8. The method of claim 7, wherein the effective dosage of the fat-soluble extract of *Brucea javanica* L. Merr is 15 mg/kg.

* * * * *